United States Patent [19]

Upsher

[11] Patent Number: 5,651,760
[45] Date of Patent: Jul. 29, 1997

[54] LARYNGOSCOPE INCLUDING MEANS FOR LOCKING THE BLADE IN AN OPERATIVE POSITION

[75] Inventor: Michael S. Upsher, Menlo Park, Calif.

[73] Assignee: Upsher Laryngoscope Corporation, Foster City, Calif.

[21] Appl. No.: 407,921

[22] Filed: Mar. 20, 1995

[51] Int. Cl.$^6$ .................................................. A61M 5/32
[52] U.S. Cl. ........................... 600/193; 600/185; 600/190; 600/196; 600/197
[58] Field of Search .................................. 600/184, 185, 600/190, 193, 196, 197, 210, 213, 226, 235, 237, 238, 239, 240

[56] References Cited

U.S. PATENT DOCUMENTS

| | | | |
|---|---|---|---|
| 2,646,037 | 7/1953 | Cook et al. | 600/193 |
| 4,384,570 | 5/1983 | Roberts | 128/4 |
| 4,437,458 | 3/1984 | Upsher . | |
| 4,557,256 | 12/1985 | Bauman | 600/193 |
| 5,381,787 | 1/1995 | Bullard | 128/11 |

Primary Examiner—Beverly M. Flanagan
Attorney, Agent, or Firm—Stephen C. Shear

[57] ABSTRACT

An improved laryngoscope and its method of use are disclosed herein. The laryngoscope includes a handle and a blade separate from the handle. The blade is engagable with the handle for selective movement between an inoperative position and an operative position. A locking mechanism is provided integrally with the laryngoscope which is selectively movable between an unlocked position, in which the blade remains movable between its inoperative and operative positions, and a locked position, in which, upon movement of the locking mechanism to the locked position while the blade is in its operative position, thereafter fixes the blade in the operative position until such time that the locking mechanism is moved to the unlocked position.

10 Claims, 4 Drawing Sheets

LARYNGOSCOPE INCLUDING MEANS FOR LOCKING THE BLADE IN AN OPERATIVE POSITION

BACKGROUND OF THE INVENTION

The present invention relates generally to a laryngoscope, and more particularly to a laryngoscope including a mechanism to selectively lock the blade to the handle in an operative position.

The use of a laryngoscope for the intubation of a patient, as well as its use in other procedures, is well known in the art. FIG. 1 illustrates a typical prior art laryngoscope, generally indicated by reference numeral 10, in use during a representative procedure. Laryngoscope 10 includes a handle 12 and a blade 14. The blade includes a handle connecting segment 16 and a tongue engaging segment 18 inserted into a patient 20, as shown in FIG. 1. The laryngoscope of FIG. 1 also includes fiber optic viewing means 22 for remote viewing of the anatomy of the patient adjacent tongue engaging segment 18.

FIG. 2, which is taken directly from U.S. Pat. No. 4,437,458, specifically shows details of the prior art arrangement of FIG. 1 relating to the connection of blade 14 to handle 12. The handle includes a crossbar pin 24 extending between a pair of parallel upright structures 26, only one of which is shown. Crossbar pin 24 is engaged by a slot 28 on handle connecting segment 16 of the blade. The crossbar pin is resiliently held to the blade by a detent 29 which is also typical in the prior art. The blade is pivotally movable about pin 24 between an inoperative position in which tongue engaging segment 18 may be moved to a position directly adjacent handle 12 (not shown) and an operative position (as depicted in FIGS. 1 and 2) in which the blade extends forward from the handle.

Referring again to FIG. 2, the blade is held in the operative position by a pair of opposing locking mechanisms 30, carried by opposing sides of the handle connecting segments of blade 14. In prior art assemblies, typical of the one illustrated here, the opposing locking mechanisms are generally identical and, for purposes of simplicity of description, only the one shown will be described herein. Locking mechanism 30 is comprised of a ball bearing 32 received in a bore 34 having a mouth 36 which is of a diameter slightly less than the diameter of the ball bearing. A spring, which is not shown, typically biases ball bearing 32 to seat against mouth 36 so that a portion of the ball extends outwardly from the blade into a recess 38 defined by upright structure 26 of the handle which opposes mouth 36. When the blade is in the operative position, the ball bearings are intended to resiliently hold the blade in position during use of the laryngoscope.

While the laryngoscope, as depicted in FIGS. 1 and 2, is generally satisfactory for its intended purpose, there is a particular aspect of the instrument as shown and described above which is improved upon by the present invention, as will be discussed below.

The particular problem with the prior art laryngoscope described above resides in the fact that the blade does not positively lock to the handle when the blade is mounted on the handle in its operative position. Opposing locking mechanisms 30 do provide a measure of retention, but it is of a resilient nature such that sufficient applied force will disengage the detents and allow the handle to move to an inoperative position adjacent the blade. This problem is particularly troublesome during withdrawal from the patient of the laryngoscope instrument of the type shown in FIG. 1 due to the fact that, as the instrument is withdrawn from the patient, considerable force must be applied to the handle in a direction which tends to disengage the locking mechanisms. Since a health care professional is generally concerned with many other aspects of the procedure being undertaken, such as, for example, separation of an intubated tube from the laryngoscope, it is undesirable for the handle to move to an inoperative position during such a procedure.

As will be seen hereinafter, the present invention provides a laryngoscope including means for positively locking the blade to the handle while the blade in its operative position.

SUMMARY OF THE INVENTION

As will be described in more detail hereinafter, a laryngoscope and method of using it are herein disclosed. This laryngoscope, like the prior art laryngoscope shown in FIGS. 1 and 2, includes a handle and a blade disengagably connectable to the handle for movement between operative and inoperative positions. However, in accordance with the present invention, the laryngoscope disclosed herein includes a locking mechanism which forms part of the handle and part of the blade and which is selectively movable between an unlocked position, in which the blade remains moveable between the operative and inoperative positions and a locked position which, upon movement to the locked position while the blade is in the operative position, thereafter selectively fixes the blade in the operative position until such time that the locking mechanism is moved to the unlocked position.

In a method of using the laryngoscope of the present invention during a procedure, the blade is first supported on the handle for movement between an operative position and an inoperative position, the blade is then moved to the operative position, and thereafter locked in the operative position prior to and throughout the duration of the procedure.

BRIEF DESCRIPTION OF THE DRAWINGS

The present invention may be understood by reference to the following detailed description taken in conjunction with the drawings, in which.

DETAILED DESCRIPTION OF THE INVENTION

Figure 2:
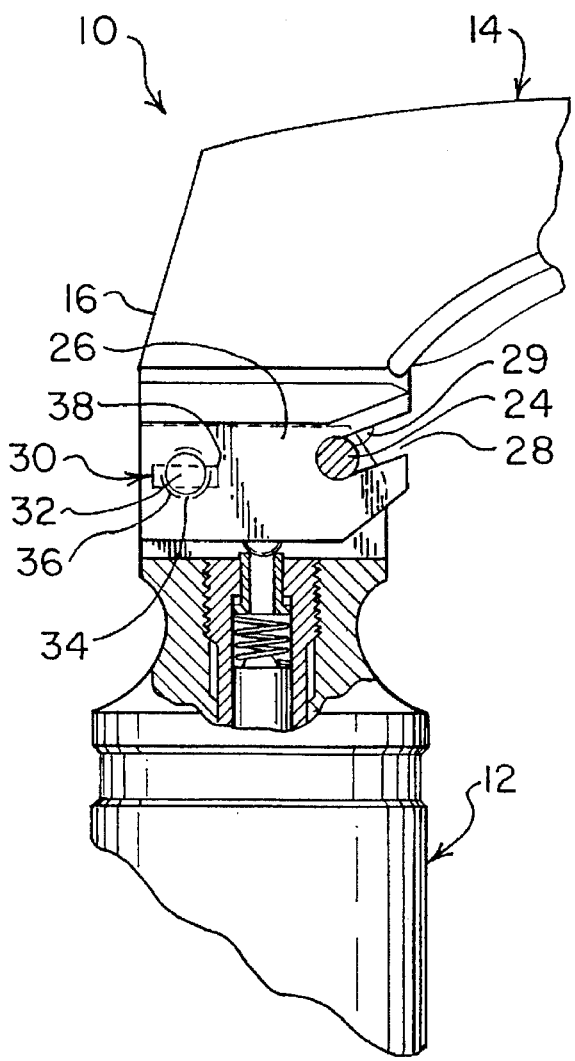
FIG. 2 is a fragmentary view of the laryngoscope of FIG. 1 illustrating details of the attachment of the blade to the handle.
Figure 1:
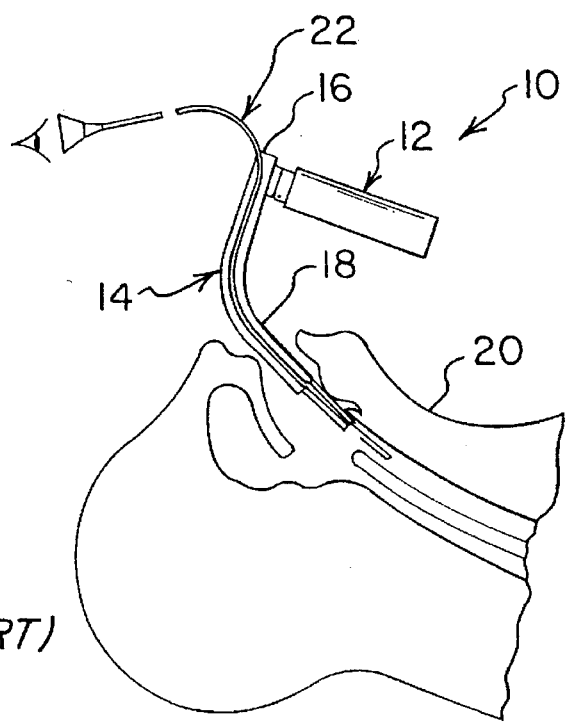
FIG. 1 illustrates a prior art laryngoscope (including a blade and a handle) in use on a patient.
Figure 3:
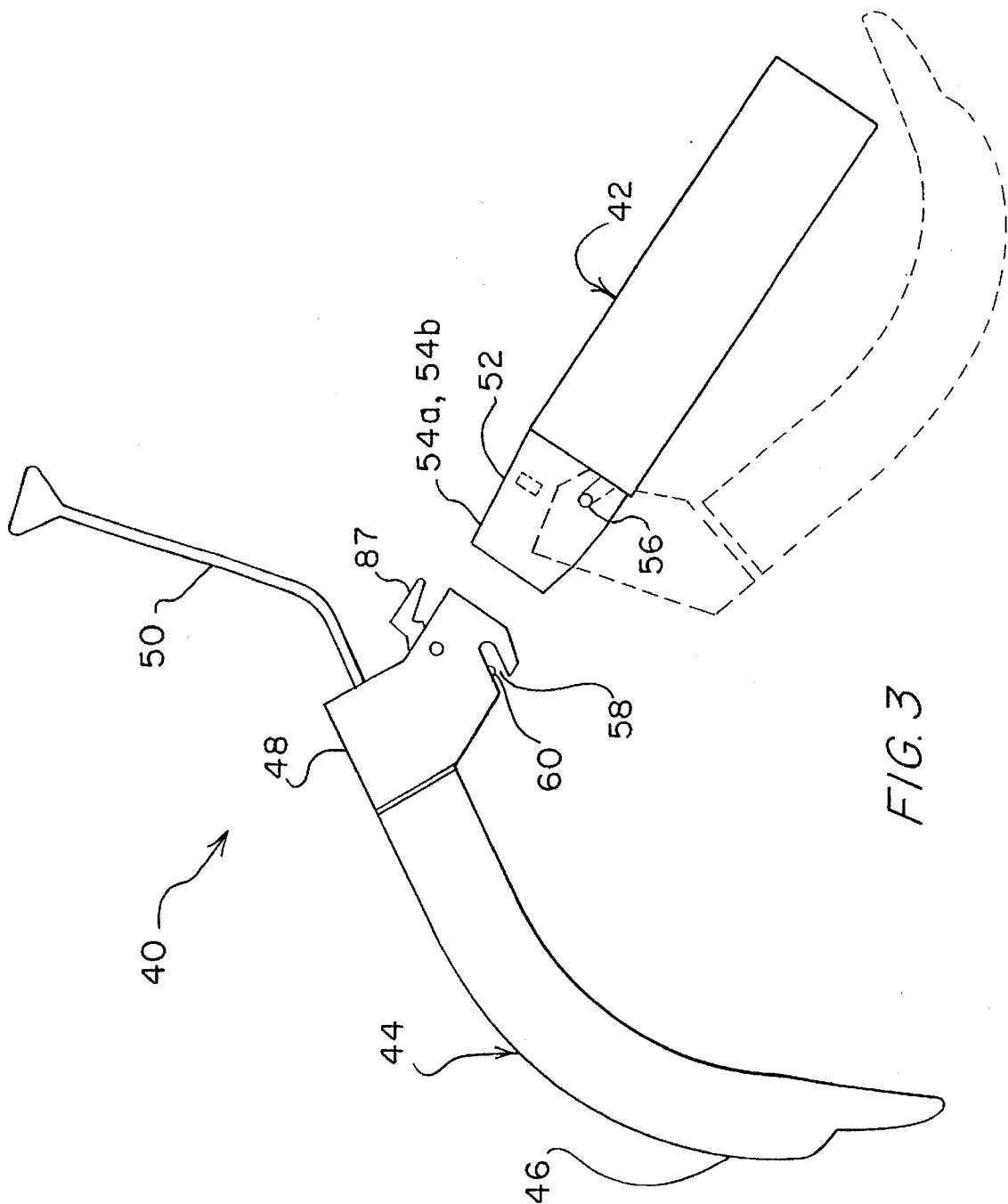
FIG. 3 is a side elevational view of a laryngoscope manufactured in accordance with the present invention showing the blade separate from the handle and the blade, in phantom, attached to the handle in an inoperative position.

Having described FIGS. 1 and 2 previously, attention is immediately directed to FIG. 3 which illustrates a laryngoscope manufactured in accordance with the present invention and generally designated by reference numeral 40. Laryngoscope 40 includes a handle 42 and a blade 44. Blade 44 includes a tongue engaging segment 46 and a handle engaging segment 48. Blade 44 also includes a fiber optic viewing means 50, typical of recent prior art laryngoscope, to allow viewing of the area of anatomy immediately in advance of tongue engaging segment 46 during use of the laryngoscope. The presence or absence of the fiber optic viewing means has no impact on the present invention and is shown here only to illustrate the present invention as embodied in a state of the art laryngoscope. The present invention is equally applicable to all types of laryngoscope in which the blade is disengagably connectable to the handle directly in its operative position or for movement between an operative and inoperative position.

Figure 4:
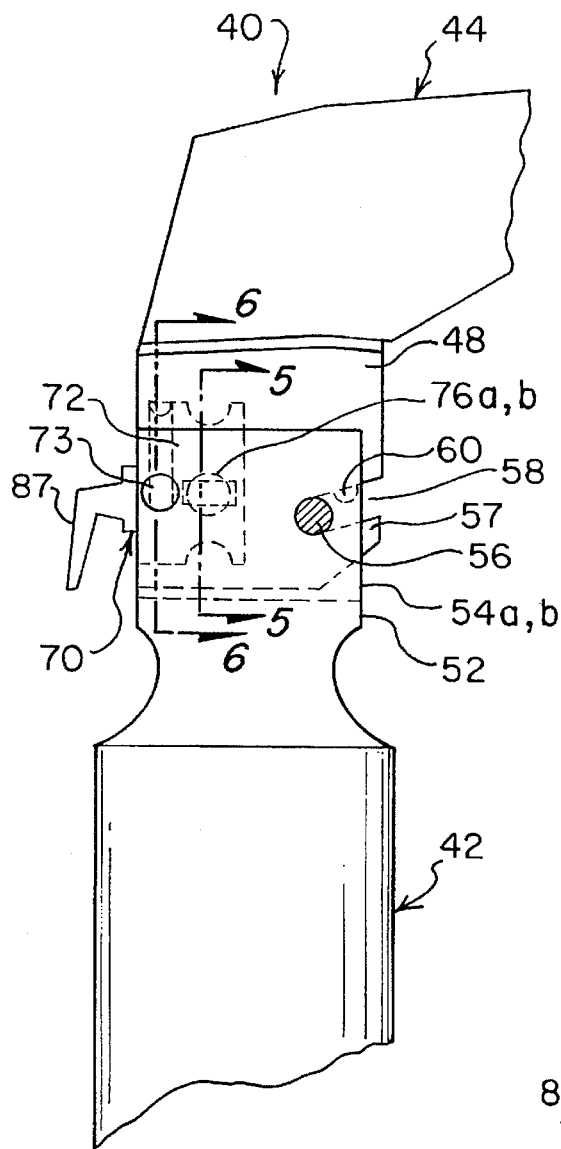
FIG. 4 is a fragmentary enlarged side elevational view of the laryngoscope of FIG. 3 illustrating details of an arrangement for receiving and locking the blade to the handle.
Figure 5:
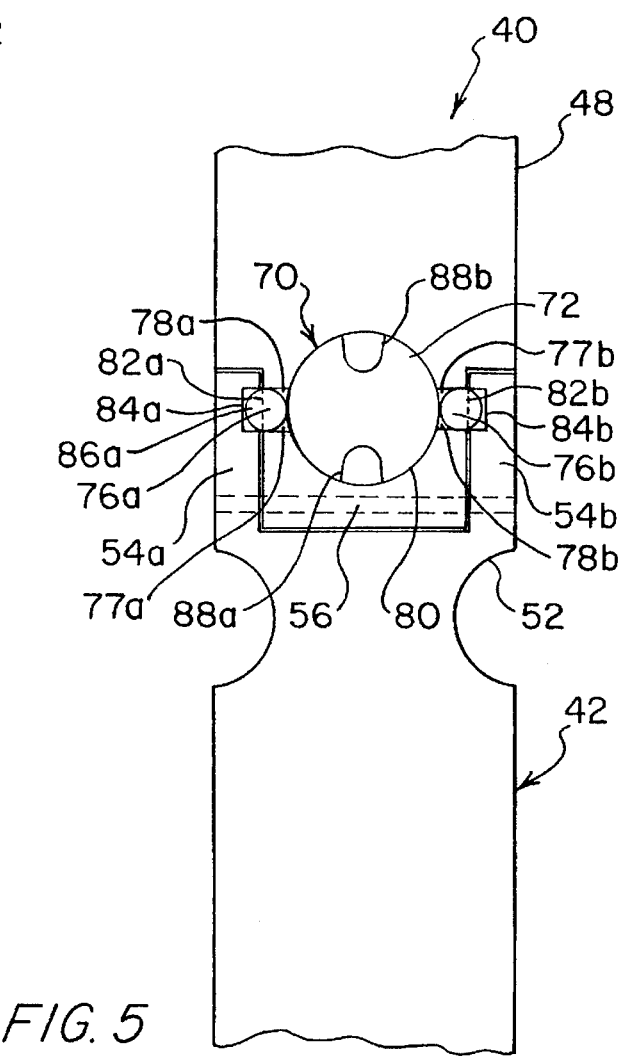
FIG. 5 is a cross-sectional view of the laryngoscope of FIG. 4 taken generally along line 5—5 in FIG. 4 to illustrate details of a locking mechanism in a locked position.

Referring now to FIG. 5 in conjunction with FIG. 4, handle 42 includes a bifurcated blade receiving segment 52 including a pair of opposing upright structures 54a and 54b. A crossbar pin 56 extends between upright structures 54a and 54b. Handle connecting segment 48 of the blade includes a jaw 57 which defines a crossbar pin receiving slot 58, visible in FIGS. 3 and 4, for mounting the blade to the handle by sliding the crossbar pin into the slot. Slot 58 includes a detent 60 for resiliently retaining the pivot pin in the slot. Once the crossbar pin is engaged with the slot the blade is moveable between an inoperative position, shown in phantom in FIG. 3, in which tongue engaging segment 46 may be brought into a position adjacent handle 42 and an operative position, as previously shown in FIG. 1.

Figure 6:
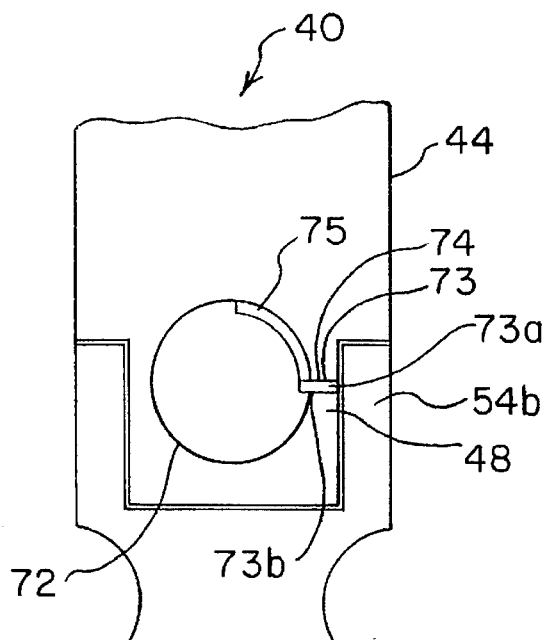
FIG. 6 is a cross-sectional view of the laryngoscope of FIG. 4 taken generally along line 6—6 in FIG. 4 to illustrate further details of the locking mechanism.
Figure 7:
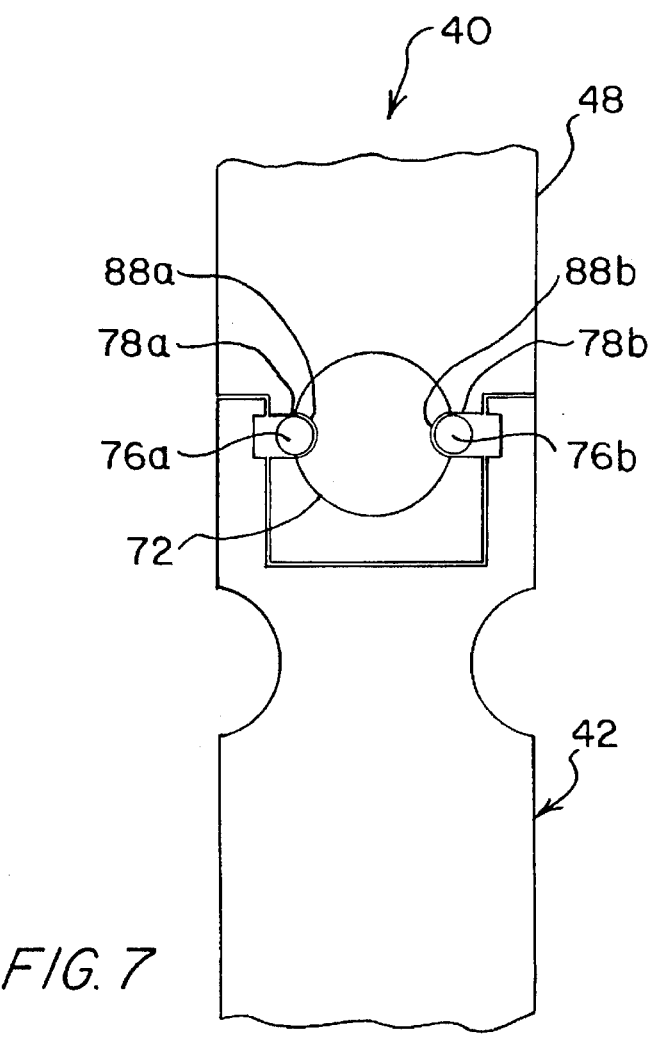
FIG. 7 is a cross-sectional view of the laryngoscope of FIG. 4 also taken generally along line 5—5 in FIG. 4 except that the locking mechanism is illustrated in an unlocked position.

Referring again to FIG. 4, and in accordance with the present invention, the handle connecting portion of the blade includes a locking mechanism generally designated by reference numeral 70. Locking mechanism 70 includes a rotatable cam 72 disposed within handle connecting portion 48 of the blade. Cam 72 is rotatable between a locked position, which is shown in FIGS. 4-6, and an unlocked position, which is shown in FIG. 7. The cam is retained within the blade by a pin 73 having opposing end portions 73a and 73b, seen most clearly in FIG. 6. The pin is fixedly attached to the blade by suitable means which may include end portion 73a thread mounted through a cooperating threaded through hole 74 in handle receiving portion 48 of the blade. Opposing end potion 73b of pin 73 is positioned so as to engage a groove 75 defined on the cam to allow rotation of the cam while still retaining it within the handle receiving portion 48 of the blade. This arrangement of the pin and groove also serves to define the limits of rotation of the cam within the handle and, in this case, is configured to provide for rotation of the cam within a predetermined range of 90 degrees, as defined by groove 75 which circumscribes a 90 degree arc on the cam. An additional pin (not shown) may be provided opposite pin 73 to further support the cam along with an associated additional groove (not shown) defined on the cam, if so desired, to further retain the cam. Many other arrangements, in addition to the example disclosed herein, may also be used to suitably retain the cam for rotation within the handle and these are all considered to be within the scope of the present invention. In a more basic embodiment, groove 75 could extend all the way around the cam, although this is not shown.

Referring again to FIG. 5, locking mechanism 70 is shown in the locked position and includes a pair of locking balls 76a and 76b, each of which is disposed in respective opposing bores 77a and 77b defined within handle receiving segment 48 of the blade. Each of bores 77a and 77b has a diameter which is slightly greater than the diameter of the locking balls to allow each ball to move freely along the length of its respective bore dependent upon the position of the cam. The bores include inner openings 78a and 78b, adjacent an outer surface 80 of cam 72, and outer mouths 82a and 82b, which have a diameter slightly less the diameter of the locking balls and align with respective locking recesses 84a and 84b defined on upright structures 54a and 54b on the blade when the blade is in the operative position. Each one of the locking balls is captured between the respective outer mouth of the bore in which it is received and the outer surface of the cam adjacent the inner opening of the bore. For example, locking ball 76a is captured in bore 77a between mouth 82a and outer surface 80. Since the diameter of mouth 82a is only slightly less than the diameter of locking ball 76a, the locking ball is seated against the mouth such that a portion 86a of the ball projects outwardly from the mouth of the bore and into recess 84a on upright structure 54a of the blade, as may be seen in FIG. 5, which also shows locking ball 76b similarly arranged, with a projecting potion 86b.

Continuing to refer to FIG. 5, if an attempt is made to move the blade to an inoperative position with the locking balls positioned as shown and just described, a shearing force is applied to each ball by the blade pivoting about crossbar 56. Since the locking balls are formed from a durable material, for example, such as stainless steel, the shearing applied to cause damage to the balls would be substantial and, in fact, in the locked position, it is very difficult to move the blade from the operative to the inoperative position, short of actually breaking some portion of the locking mechanism. Conversely, in the unlocked position, which will be described immediately hereinafter, movement of the blade relative to the handle is accomplished with ease.

A locking handle or actuator 87, shown in FIG. 3 and again in FIG. 4, is provided as a portion of locking mechanism 70, which may be formed integrally with cam 72 or attached as a separate part formed from a suitable material, for selective rotation of the cam between the unlocked and locked positions. As the cam is rotated in response to rotation of the locking handle, from the locked to the unlocked position, outer cam surface 80 moves in relation to locking balls 76a and 76b to rotate a pair of opposing recesses 88a and 88b defined by outer surface 80 of the cam, as shown in the cross-sections of FIGS. 5 and 6.

Referring now to FIG. 7, when locking mechanism 70 is rotated to the unlocked position, the cam is correspondingly positioned such that opposing recesses 88a and 88b are brought into alignment with respective inner openings 78a and 78b of the bores receiving the locking balls. Recesses 88a and 88b are profiled so as to at least partially receive each locking ball in the unlocked position to an extent sufficient to insure that the ball will not positively engage respective opposing locking recess 84a or 84b so that the blade is easily movable between the inoperative and operative positions, in accordance with the present invention. It is noted here that the locking mechanism is selectively and repeatably movable between the unlocked and locked positions while the blade is in the operative position on the handle.

The laryngoscope of the present invention may be constructed from a variety of materials suitable for use in medical instruments, for example, such as stainless steel or a variety of plastics. It is also anticipated, particularly with regard to construction of the laryngoscope from plastic, that separate disposable blade and handle units will be available. In addition, a laryngoscope blade including a locking mechanism, in accordance with the present invention, may be provided for use in cooperation with standard laryngoscope handles, which are currently in use.

In the method of using the laryngoscope of the present invention, initially, prior to use of the laryngoscope, the handle is typically separated from the blade, as depicted in FIG. 3. To use the laryngoscope, crossbar pin 56 on the blade must first be engaged with crossbar pin receiving slot 58 on blade connecting segment 48 of the blade. The pin is brought past detent 60 to seat the pin in the slot with the blade in the inoperative position, shown in phantom in FIG. 3. The blade is next moved to the operative position with locking mechanism 70 in the unlocked position, as shown in FIG. 7. In accordance with the present invention, once the blade is in the operative position, locking handle 87 is moved to the locked position to positively lock the blade to the handle, as described above, and shown in FIGS. 4 and 5. The laryngoscope is then used in the locked position throughout any applicable procedure and, upon completion of the procedure, the locking mechanism may be moved to the unlocked position, the blade moved to an inoperative position with respect to the handle and, finally, the blade disengaged from the handle.

Since a locking mechanism for locking a laryngoscope blade to a laryngoscope handle, while the handle is in an operative position, may be realized in a variety of ways, including, for example, providing a locking mechanism carried primarily by the handle, it should be understood that the present invention may be embodied in many other specific forms without departing from the spirit or scope of the invention. For example, while the locking mechanism is actuated by rotary motion, it could be actuated in other ways, for example, by means of linear and/or push-pull motion. Therefore, the present examples and methods are to be considered as illustrative and not restrictive, and the invention is not to be limited to the details given herein, but may be modified within the scope of the appended claims.

What is claimed is:

1. A laryngoscope, comprising:
   a) a handle;
   b) a blade separate from said handle including a tongue engaging segment and a handle engaging segment; and
   c) engagement means forming part of the handle and part of the handle engaging segment on the blade for engaging the blade to the handle such that the blade is movable between an inoperative position and an operative position while remaining engaged with the handle, said engagement means including locking means movable between an unlocked position, in which the blade remains moveable between its inoperative and operative positions, and a locked position which, upon movement of said locking means to the locked position while the blade is in its operative position, thereafter locks the blade in the operative position until such time that the locking means is moved to the unlocked position, said locking means including
      i) a pair of opposing locking members carried by the blade for movement between locking positions in which the locking members each engage respective predetermined portions of the handle and unlocking positions disengaged from said predetermined portions when the blade is in its operative position, and
      ii) actuator means for selectively moving the locking members from their disengaged positions to their engaged positions when the blade is in its operative position and for holding the locking members in their engaged positions such that the locking members cooperate with the respective predetermined portions of the handle to prevent relative movement between the blade and the handle.

2. A laryngoscope in accordance with claim 1 wherein said predetermined portions each define a respective recess and wherein each one of the locking members extends outwardly from the blade and is locked into a respective one of the recesses of said predetermined portions when the actuator means is in its locked position and said locking member is in its engaged position.

3. A laryngoscope in accordance with claim 1 wherein the blade defines a pair of opposing bores as a portion of said locking means and each one of the locking members is received for movement in a respective one of the bores.

4. A laryngoscope in accordance with claim 1 wherein the locking members are balls.

5. A laryngoscope in accordance with claim 1 wherein said actuator means includes cam means disposed within the blade and selectively rotatable between said unlocked position and said locked position, said cam means cooperating with and arranged to move said locking members from said disengaged position to said engaged position in response to corresponding rotational movement of the cam means between said unlocked and said locked positions.

6. A laryngoscope in accordance with claim 5 wherein the blade defines a pair of opposing bores as a part of the locking means, each having a predetermined diameter, an inner opening adjacent said cam means and an outer opening which is smaller in diameter than said predetermined diameter, the locking means further including a pair of balls with each respective ball having a diameter greater than that of said outer opening and smaller than the predetermined diameter, said balls functioning as said locking members by each ball being received in one of said respective bores to be captured between the outer opening and the cam means, the cam means configured to allow the balls, in the unlocked position, to remain in said disengaged position and, in the locked position, to move and hold the balls against the outer opening of each respective bore such that a portion of each ball extends outward from the blade to engage said respective predetermined portions of the handle while the blade is in said operative position, whereby to selectively lock the blade to the handle in the operative position.

7. A laryngoscope in accordance with claim 5 including a pin having one end fixedly attached to said blade and an outer end extending toward said cam means, said cam means defining a retaining groove thereon for receiving said outer end of the pin to provide for rotation of the cam means with respect to the blade while retaining the cam means within the latter.

8. A laryngoscope, comprising:
   a) a handle defining an opposing pair of engagement recesses;
   b) a blade separate from said handle including a tongue engaging segment and a handle engaging segment;
   c) means forming part of said handle and part of said blade for engaging said handle engaging segment of the blade to the handle for movement between an inoperative position and an operative position; and
   d) a locking mechanism forming part of the blade, said locking mechanism including
      i) a pair of balls having a predetermined diameter, a pair of opposing bores defined by the blade and having a diameter greater than that of the predetermined diameter of the balls, an inner opening and an outer opening smaller in diameter than the predetermined diameter of the balls, ii) cam means rotatably received within the blade for selective rotation between an unlocked position and a locked position, said cam means defining a retaining groove and including opposing cam surfaces adjacent each said respective inner opening, each respective one of said balls captured in a respective one of the bores between the outer opening and one of the cam surfaces such that, in the unlocked position the balls are disengaged from the handle and, in the locked position, the cam surfaces hold each respective ball in an engaged position against each respective outer opening to project outwardly from the opening into the cooperating engagement recess in the handle which is aligned with the respective outer opening while the blade is in the operative position to hold the blade in the operative position until the cam means is selectively rotated to the unlocked position, iii) a cam retaining pin fixedly attached at one end to the blade and including another end positioned within the retaining groove on the cam means to permit rotation of the cam means while retaining the cam means within the blade.

9. A laryngoscope, comprising:

a) a handle;

b) a blade separate from said handle including a tongue engaging segment and a handle engaging segment;

c) engagement means forming part of the handle and part of the handle engaging segment on the blade for engaging the blade to the handle such that the blade is movable between an inoperative position and an operative position while remaining engaged with the handle;

d) at least one locking member carried by the blade for movement between a locked position and an unlocked position which, upon movement of said locking member to the locked position while the blade is in its operative position, thereafter locks the blade in the operative position by engaging a recess defined by said handle, said locking member extending outwardly from the blade and into said recess until such time that the locking member is moved to said unlocked position away from said recess; and e) actuator means for selectively moving the locking member from its unlocked position to and holding it in its locked position such that the locking member extends into said recess while the blade is in the operative position to prevent relative movement between the blade and the handle.

10. A laryngoscope, comprising:

a) a handle;

b) a blade separate from said handle including a tongue engaging segment and a handle engaging segment;

c) engagement means forming part of the handle and part of the handle engaging segment on the blade for engaging the blade to the handle such that the blade is movable between an inoperative position and an operative position while remaining engaged with the handle; and d) locking means forming part of said engagement means for movement between an unlocked position, in which the blade remains moveable between its inoperative and operative positions, and a locked position which, upon movement of said locking means to the locked position while the blade is in its operative position, thereafter locks the blade in the operative position until such time that the locking means is moved to the unlocked position, said locking means including i) a pair of ball bearings, ii) means supporting the ball bearings for movement between unlocked and locked positions, and iii) cam means movable between unlocked and locked positions such that when the cam means and ball bearing are in the locked positions the blade is locked in place relative to the handle while the blade is in the operative position.

* * * * *